United States Patent
Kruecker (10) Patent No.: US 11,484,288 B2
(45) Date of Patent: Nov. 1, 2022

(54) WORKFLOW, SYSTEM AND METHOD FOR MOTION COMPENSATION IN ULTRASOUND PROCEDURES

(71) Applicant: KONINKLIJKE PHILIPS N.V., Eindhoven (NL)

(72) Inventor: Jochen Kruecker, Andover, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 463 days.

(21) Appl. No.: 16/612,386

(22) PCT Filed: May 7, 2018

(86) PCT No.: PCT/EP2018/061636
§ 371 (c)(1),
(2) Date: Nov. 10, 2019

(87) PCT Pub. No.: WO2018/206473
PCT Pub. Date: Nov. 15, 2018

(65) Prior Publication Data
US 2020/0196983 A1 Jun. 25, 2020

Related U.S. Application Data

(60) Provisional application No. 62/504,571, filed on May 11, 2017.

(51) Int. Cl.
*A61B 8/00* (2006.01)
*A61B 34/20* (2016.01)
(Continued)

(52) U.S. Cl.
CPC .......... *A61B 8/4254* (2013.01); *A61B 34/20* (2016.02); *G06T 7/0012* (2013.01); *G06T 7/337* (2017.01);
(Continued)

(58) Field of Classification Search
CPC .............. A61B 8/4254; A61B 34/20; A61B 2034/2051; A61B 2034/2063;
(Continued)

(56) References Cited

U.S. PATENT DOCUMENTS 8,885,897 B2   11/2014  Xu et al.
9,019,262 B2    4/2015  Ma et al.
(Continued)

FOREIGN PATENT DOCUMENTS

EP    2131326 A2    12/2009
WO    2012098483 A1   7/2012
(Continued)

OTHER PUBLICATIONS

De Silva et al: "Improving 2D-3D Registration Optimization Using Learned Prostate Motion Data"; MICCAI 2013, pp. 124-131.
(Continued)

*Primary Examiner* — Joel Lamprecht (57) ABSTRACT

An ultrasound imaging device (10) with an ultrasound probe (12) acquires a live ultrasound image which is displayed with a contour (62) or reference image (60) registered with the live ultrasound image using a composite transform (42). To update the composite transform, the ultrasound imaging device acquires a baseline three-dimensional ultrasound (3D-US) image (66) tagged with a corresponding baseline orientation of the ultrasound probe measured by a probe tracker, and one or more reference 3D-US images (70) each tagged with a corresponding reference orientation. Transforms (54) are computed to spatially register each reference 3D-US image with the baseline 3D-US image. A closest reference 3D-US image is determined whose corresponding orientation is closest to a current orientation of the ultrasound probe as measured by the probe tracker. The composite transform is updated to include the transform to (Continued)

spatially register the closest reference 3D-US image to the baseline 3D-US image.

15 Claims, 4 Drawing Sheets

(51) Int. Cl.
*G06T 7/33* (2017.01)
*G06T 7/37* (2017.01)
*G06T 7/00* (2017.01)

(52) U.S. Cl.
CPC ........ *G06T 7/37* (2017.01); *A61B 2034/2051* (2016.02); *A61B 2034/2063* (2016.02); *G06T 2207/10088* (2013.01); *G06T 2207/10136* (2013.01); *G06T 2207/30081* (2013.01); *G06T 2211/428* (2013.01)

(58) Field of Classification Search
CPC ......... G06T 7/0012; G06T 7/337; G06T 7/37; G06T 2207/10088; G06T 2207/10136; G06T 2207/30081; G06T 2211/428; G06T 7/30; G06T 2207/10132
See application file for complete search history.

(56) References Cited

U.S. PATENT DOCUMENTS

| | | |
|---|---|---|
| 9,526,476 B2 | 12/2016 | Schwartz et al. |
| 2009/0303252 A1* | 12/2009 | Hyun ............... A61B 6/032 345/643 |
| 2010/0268085 A1* | 10/2010 | Kruecker .......... G01S 7/52074 600/443 |
| 2018/0146955 A1* | 5/2018 | Kruecker .......... A61B 8/5246 |

FOREIGN PATENT DOCUMENTS

| | | |
|---|---|---|
| WO | 2013084094 A1 | 6/2013 |
| WO | 2014087324 A1 | 6/2014 |
| WO | 2016178198 A1 | 11/2016 |
| WO | 2017017556 A1 | 2/2017 |

OTHER PUBLICATIONS

De Silva et al: "Evluating the Utility of 3D Trus Image Information in Guiding Intra-Procedure Registration for Motion Compensation"; Proc. of SPIE, vol. 9036, 2014, pp. 90361B-1-90361B-6.

Krucker et al: "Fusion of Realtime Transrectal Ultrasound With Pre-Acquired MRI for Multi-Modality Prostate Imaging"; Proc. of SPIE, vol. 6509, 2007, pp. 650912-1-650912-12.

Talou et al: "Combining Transveral and Logitudinal Registration in IVUS Studies":MICCAI 2015, Part II, LNCS 9350, pp. 346-353, 2015.

Xu et al: "Closed-Loop Control I Fused MR-TRUS Image-Guided Prostate Biopsy"; MICCAI 2007, Part I, LNCS 4791, pp. 128-135, 2007.

PCT/EP2018/061636 ISR & WO, Aug. 21, 2018, 14 Page Document.

* cited by examiner

WORKFLOW, SYSTEM AND METHOD FOR MOTION COMPENSATION IN ULTRASOUND PROCEDURES

CROSS-REFERENCE TO PRIOR APPLICATIONS

This application is the U.S. National Phase application under 35 U.S.C. § 371 of International Application No.PCT/EP2018/061636, filed on May 7, 2018, which claims the benefit of U.S. Provisional Patent Application No. 62/504,571, filed on May 11, 2017. These applications are hereby incorporated by reference herein.

FIELD

The following relates generally to the imaging-guided surgical arts such as biopsy arts, brachytherapy arts, and the like, to ultrasound imaging performed to provide imaging guidance in such surgical procedures, and the like.

BACKGROUND

Imaging-guided surgical procedures are used for diverse purposes such as tissue sample extraction (i.e. biopsy) procedures, targeted laser ablation procedures, and brachytherapy procedures (in which radioactive seeds are delivered to targeted locations). Ultrasound (US) imaging is a common modality for image guidance of surgical procedures such as rectal prostate biopsy or brachytherapy procedures. In these procedures, a rectal US probe is employed, and a grid may be used to align the biopsy needle or other interventional instrument. To obtain (near) real-time imaging, two-dimensional (2D) US imaging (commonly referred to as "live" 2D-US imaging) is commonly employed. 3D-US live imaging may also be employed if imaging speed is sufficient. To register the live US images in space, tracking of the US probe is performed, for example by electromagnetic (EM) tracking, optical tracking (if the probe is external to the patient), or so forth. Further, a pre-operative three-dimensional (3D) US baseline image is acquired to provide contouring of the prostate or other anatomical feature(s) of interest in 3D space. In some procedures, a three-dimensional (3D) planning image is acquired by another modality such as magnetic resonance imaging (MRI) or computed tomography (CT), the contouring is done in the planning image and the 3D US baseline image is used as an intermediary to register the planning image (or the contour defined in the planning image) to the live 2D-US image. In the latter case, the planning image is usually acquired prior to the image-guided surgical procedure to provide information for identifying tumors or other biopsy targets, contouring the prostate organ.

Some illustrative approaches are disclosed in Xu et al., U.S. Pat. No. 8,885,897. In one such illustrative approach, a pre-operative baseline 3D-US image is compared with a 3D diagnostic image (e.g. 3D-MRI) to determine a baseline transform which registers the baseline 3D-US and 3D-MRI volume images. During the surgical procedure, live 2D (or 3D) US images are acquired. One or a group of the live US images are compared with the baseline 3D-US image to determine a motion correction transform. An image adjustment operates on the 3D-MRI image with the baseline transform and the motion correction transform to generate a motion corrected 3D-MRI image that is displayed together with (e.g. fused with) the display of the live US image. In this way, tissue motion (i.e. distortion or change) that may have occurred between acquisition of the 3D-MRI image and the subsequent live US imaging is compensated.

The following discloses new and improved systems and methods.

SUMMARY

In one disclosed aspect, an interventional imaging device includes an ultrasound probe, an ultrasound imaging device operatively connected with the ultrasound probe to perform ultrasound imaging using the ultrasound probe, a display, and a probe tracker (28) operative to track orientation of the ultrasound probe. The device further includes an electronic processor operatively connected with the ultrasound imaging device, the probe tracker, and the display. A non-transitory storage medium stores instructions readable and executable by the electronic data processor to operate the ultrasound imaging device to acquire a live ultrasound image and to operate the display to display the live ultrasound image together with a contour or reference image that is registered with the live ultrasound image using a composite transform, and to perform further operations including: operating the ultrasound imaging device to acquire a baseline three-dimensional ultrasound (3D-US) image tagged with a corresponding baseline orientation of the ultrasound probe measured by the probe tracker for the baseline 3D-US image; operating the ultrasound imaging device to acquire one or more reference 3D-US images each tagged with a corresponding reference orientation of the ultrasound probe measured by the probe tracker for the reference 3D-US image; computing a transform to spatially register each reference 3D-US image with the baseline 3D-US image; determining a closest reference 3D-US image whose corresponding orientation is closest to a current orientation of the ultrasound probe measured by the probe tracker; and updating the composite transform to include the transform to spatially register the closest reference 3D-US image to the baseline 3D-US image.

In another disclosed aspect, a non-transitory storage medium stores instructions readable and executable by an electronic processor that is in operative communication with an ultrasound imaging device with an ultrasound probe and with a display and with a probe tracker operative to track orientation of the ultrasound probe. The instructions are readable and executable by the electronic processor to perform a live imaging method including: operating the ultrasound imaging device to acquire a live ultrasound image; spatially registering a contour or reference image with the live ultrasound image using a composite transform; displaying the live ultrasound image together with the spatially registered contour or reference image on the display; and adjusting the composite transform. The adjustment is by operations including: operating the ultrasound imaging device to acquire a baseline three-dimensional ultrasound (3D-US) image tagged with a corresponding baseline orientation of the ultrasound probe measured by the probe tracker for the baseline 3D-US image; operating the ultrasound imaging device to acquire one or more reference 3D-US images each tagged with a corresponding reference orientation of the ultrasound probe measured by the probe tracker for the reference 3D-US image; computing a set of transforms $\{T_{1,i}\}_{i=1,\ldots,N}$ to spatially register the reference 3D-US images with the baseline 3D-US image where N is the number of reference 3D-US images and the transform $T_{1,i}$ spatially registers the reference 3D-US image indexed by i with the baseline 3D-US image; determining a closest reference orientation which is closest to a current orientation of the ultrasound probe measured by the probe tracker; and updating the composite transform to a product of at least a transform $T_{1,k}$ and a transform $T_{2,k}$ where k indexes the determined closest reference 3D-US image whereby the transform $T_{1,k}$ spatially registers the determined closest reference 3D-US image indexed by k with the baseline 3D-US image and the transform $T_{2,k}$ spatially registers the determined closest reference 3D-US image with the live ultrasound image.

In another disclosed aspect, a live ultrasound imaging method is disclosed. An ultrasound imaging device is operated to acquire a time series of live ultrasound images using an ultrasound probe. A contour or reference image is spatially registered with the time series of live ultrasound images using a composite transform. The time series of live ultrasound images is displayed together with the spatially registered contour or reference image. The composite transform is adjusted by operations including: operating the ultrasound imaging device to acquire a baseline three-dimensional ultrasound (3D-US) image tagged with a corresponding baseline orientation of the ultrasound probe measured by a probe tracker for the baseline 3D-US image; operating the ultrasound imaging device to acquire one or more reference 3D-US images each tagged with a corresponding reference orientation of the ultrasound probe measured by the probe tracker for the reference 3D-US image; computing a set of transforms $\{T_{1,i}\}_{i=1,\ldots,N}$ to spatially register the reference 3D-US images with the baseline 3D-US image where N is the number of reference 3D-US images and the transform $T_{1,i}$ spatially registers the reference 3D-US image indexed by i with the baseline 3D-US image; determining a closest reference orientation which is closest to a current orientation of the ultrasound probe measured by the probe tracker; and updating the composite transform to a product of at least a transform $T_{1,k}$ and a transform $T_{2,k}$ where k indexes the determined closest reference 3D-US image whereby the transform $T_{1,k}$ spatially registers the determined closest reference 3D-US image indexed by k with the baseline 3D-US image and the transform $T_{2,k}$ spatially registers the determined closest reference 3D-US image with the live ultrasound image. The updated composite transform is used in the spatially registering of the contour or reference image with live ultrasound images of the time series of live ultrasound images acquired after the current live ultrasound image One advantage resides in providing live ultrasound (US) imaging in the context of a baseline 3D-US image and/or an earlier-acquired 3D-MRI or other planning image, with improved correction of the baseline 3D-US or 3D-MRI image for tissue motion that may have occurred before or during the image-guided surgical procedure.

Another advantage resides in providing live US imaging in the context of one or more organ contours or other image features delineated in a baseline 3D-US image and/or an earlier-acquired 3D-MRI or other planning image, with improved correction of the image feature(s) for tissue motion that may have occurred before or during the image-guided surgical procedure.

Another advantage resides in providing live US imaging guidance for an image-guided surgical procedure with improved robustness against tissue deformation produced by repositioning of the ultrasound probe.

Another advantage resides in providing live US imaging guidance for an image-guided surgical procedure with improved accuracy when the US probe is moved to different orientations to provide optimal viewing perspective for visualization of the surgical procedure.

Another advantage resides in providing one or more of the foregoing benefits with concomitant rapid live US imaging and consequently improved live image guidance for an image-guided surgical procedure.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

The accuracy and robustness of image registration-based motion compensation depends on the similarity of the images being registered. In some US-guided surgical procedures, the orientation of the US probe may be adjusted by the surgeon during the procedure to provide a preferred vantage point for viewing the surgery. This can create substantially different tissue deformation when compared with the baseline US image, and thus make registration between the dissimilar live US and baseline 3D-US images obtained with different probe orientation challenging. Such registration is especially difficult in the case of live 2D-US images due to the reduced image information in the 2D-US image upon which to base the registration.

Approaches disclosed herein in recognition of this problem provide a plurality of reference 3D-US images acquired with different ultrasound probe orientations. One of these is designated as the baseline 3D-US image. Each reference 3D-US image and the baseline 3D-US image is tagged with its probe orientation, that is, with the orientation of the ultrasound probe at the time the 3D-US reference or baseline image was acquired. Each reference 3D-US image is spatially registered with the baseline 3D-US image. If a different-modality planning image is also provided (for example, a 3D-MRI image or a 3D-CT image), it is spatially registered with the designated baseline image using cross-modality spatial image registration. As the interventional (i.e. surgical) procedure progresses, it is monitored using the ultrasound imaging device, which acquires live US images at a rate sufficient to provide (near) real-time imaging of the prostate or other surgical area. Typically, the live US images are two-dimensional (2D) images, although 3D live US images are contemplated if 3D-US acquisition speed is sufficient (e.g., if a 3D-US probe is employed).

Initially, the baseline 3D-US image is used for superimposing the surgically relevant contour(s) (e.g. prostate contour) and/or fusing the live US image with the planning image or a contextual 3D-US image. Alternatively, as the tracking system tracks the US probe orientation during the live US imaging, this orientation can be used to initially select the closest reference or baseline 3D-US image for this purpose. If a reference 3D-US image is selected, then the superimposition of the relevant contour(s) and/or fused 3D image entails spatially transforming using both a transform between the live US image and the closest reference 3D-US image and the initially generated transform between closest reference 3D-US image and the baseline 3D-US image.

This live tracking with contour superimposition and/or 3D image fusion continues as the interventional procedure proceeds. However, if the surgeon adjusts positioning of the US probe by a sufficiently large amount, the employed transform will become increasingly inaccurate since the presumed similarity between US probe orientation used for acquiring the live US image and the closest reference or baseline 3D-US image will become more dissimilar. As this continues, the surgeon may be expected to notice increasingly poor alignment between the live US image and the superimposed contour(s) and/or fused 3D image. At this point, the surgeon may press a trigger button or other user input to trigger an update of the spatial registration. In this update procedure, the tracking system determines the current US probe orientation for live US imaging, and this orientation is compared with the tagged US probe orientations of the baseline and reference 3D-US images to select the closest 3D-US image. The transforms are updated accordingly (e.g. a new closest reference 3D-US image is selected, the transform between new closest reference 3D-US image and the baseline 3D-US image is chosen for subsequent use, and thereafter the live US image is registered with the new closest reference 3D-US image.

In this way, motion (e.g. differential tissue deformation) caused by the surgeon repositioning the US probe is accounted for more accurately. This is done in a computationally efficient manner, because the computationally costly cross-modality registration between the planning image (e.g. 3D-MRI or 3D-CT image) and the baseline 3D-US image is not re-computed, and likewise the less computationally costly (but still somewhat costly) transforms between the reference 3D-US images and the baseline 3D-US image are not re-computed.

In some variant embodiments, contrary to this last advantage there may be an option (e.g. selectable by the surgeon or automatically triggered by an unacceptable value of a spatial registration quality metric) to acquire one or more additional reference 3D-US image(s) and/or to re-acquire a previously acquired reference 3D-US image and to compute (or re-compute) the transform(s) between the newly acquired reference 3D-US image(s) and the baseline 3D-US image. This variant approach, if employed, provides a mechanism to correct for larger motion (e.g. greater tissue deformation) or for repositioning of the US probe to a position far from any of the orientations of the reference 3D-US images by updating the reference 3D-US image(s).

Figure 1:
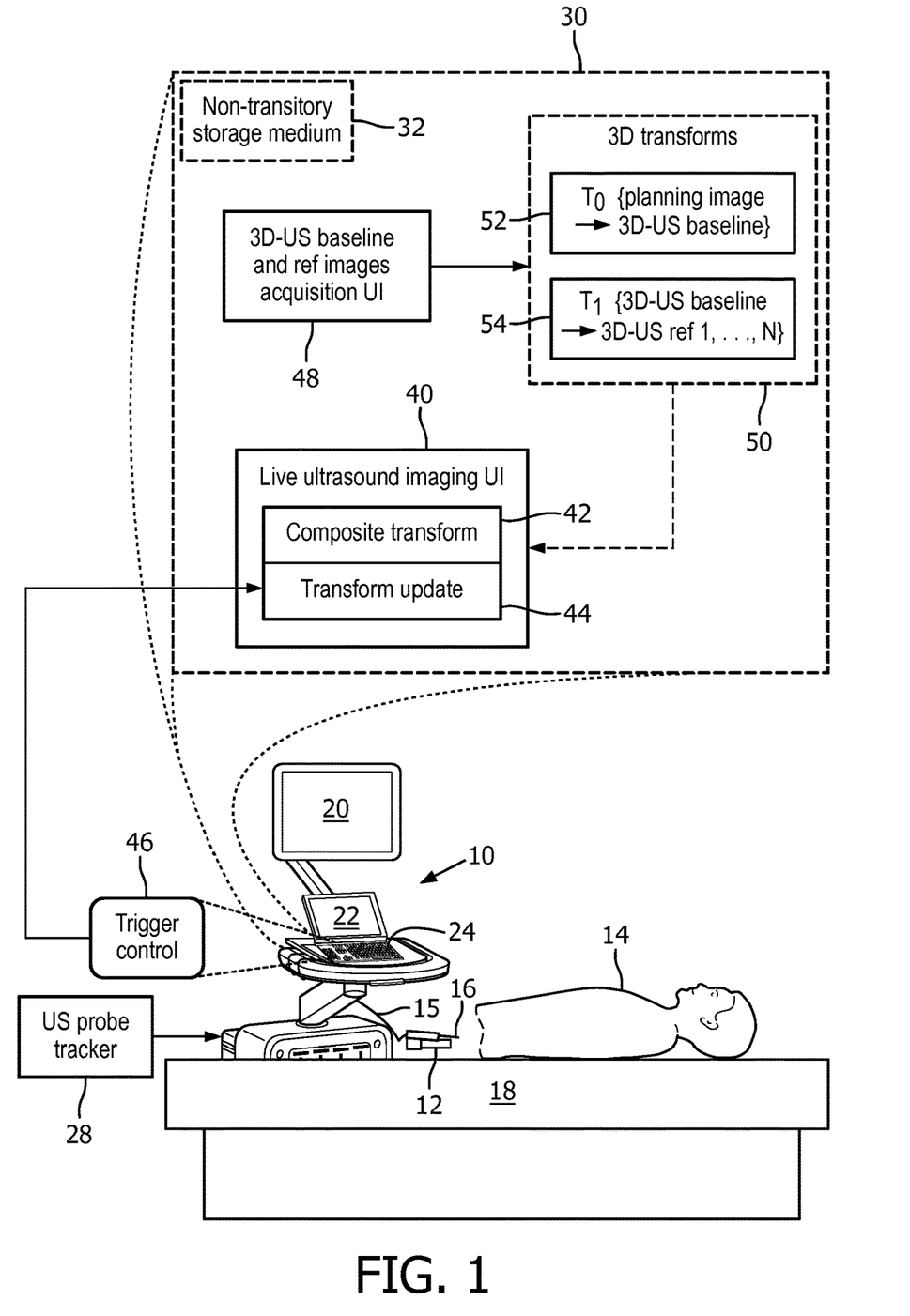
FIG. 1 diagrammatically shows an illustrative ultrasound (US)-guided prostate biopsy system.

With reference to FIG. 1, an illustrative interventional imaging device suitable for implementing the foregoing is shown. An ultrasound (US) imaging device 10 may, for example, be an EPIQ™ ultrasound imaging system available from Koninklijke Philips N.V., Amsterdam, the Netherlands, or may be another commercial or custom-built ultrasound imaging system. The ultrasound imaging device 10 is operatively connected with an US probe 12 to perform ultrasound imaging using the ultrasound probe 12. The illustrative US probe is a rectal ultrasound probe 12 which is inserted into the rectum of a patient 14. (The lower half of the patient is cut away in diagrammatic FIG. 1 to reveal the inserted probe 12 which would otherwise be occluded from view. Typically, the patient is lying on the side or facing up with the legs lifted up and fixed on a table extension.) The illustrative choice of a rectal US probe 12 is a conventional choice for US monitoring of a prostate procedure; more generally, the disclosed interventional imaging approaches may be used with other types of US probes and/or for monitoring other types of interventional surgical procedures, e.g. the US probe may be a transcutaneous US probe used in monitoring a liver or breast procedure. The illustrative ultrasound probe 12 is connected with the ultrasound imaging system 10 via cabling 15. The illustrative rectal ultrasound probe 12 for use in a prostate procedure includes an integrated biopsy needle assembly 16 for collecting biopsy samples. More generally, any type of image-guided biopsy technique may be employed, e.g. a transrectal ultrasound-guided biopsy using the integral probe 12, 16 as illustrated in which the ultrasound probe is inserted into the rectum and accesses the prostate via the rectal wall; or a transperineal biopsy in which the ultrasound probe is passed into the rectum but the biopsy needle passes through the perineum to access the prostate (optionally using a stereotactic grid plate or the like); or so forth. In some interventional procedures, the biopsy needle or other interventional instrument(s) may not be connected with the US probe. For the illustrative transrectal prostate biopsy procedure, the patient 14 lies on his side (as diagrammatically indicated in FIG. 1) on a diagrammatically indicated patient bed or support 18 with suitable pillows or other supports (not shown). The illustrative ultrasound imaging system 10 includes a display 20 for displaying ultrasound images, and one or more user interfacing components such as a user interface display 22 and user control panel 24 including user input devices such as a keyboard, dedicated buttons, a trackball or mouse or other pointing device, or so forth. Instead of or in addition to a pointing device, one or both display components 20, 22 may be a touchscreen display enabling user input by pressing a location on the display 20.

With continuing reference to FIG. 1, the interventional imaging device further includes a probe tracker 28 that is operative to track orientation of the US probe. The probe tracker 28 may, for example, comprise an electromagnetic (EM) tracker such as the Aurora® EM tracking system available from Northern Digital Inc. (NDI, Ontario, Canada). An EM tracker employs EM sensors on tracked components, e.g. one or more EM sensors (not shown) are suitably mounted on or in the US probe 12 to enable tracking its position and orientation. In other embodiments, the probe tracker may comprise a gyroscope sensor, a coordinate measurement machine (CMM) having an end attached to the US probe and a base secured to a reference point, or so forth. In other contemplated embodiments in which the US probe is visible, e.g. a transcutaneous US probe disposed external of the patient, the probe tracker 28 may utilize optical tracking using optical reflectors or the like mounted on the US probe 12, or a range camera. Fiber optic shape sensing and localization in which fiber Bragg gratings, Raleigh scattering or the like is used determine a shape, position or orientation of an optical fiber and from that data, a position or orientation of the ultrasound probe, may also be used. These are merely illustrative examples. In the illustrative examples described herein, the probe tracker 28 is assumed to be an EM tracker.

With continuing reference to FIG. 1, the interventional imaging device further includes an electronic processor 30 that is operatively connected with the US imaging device 10 and the display 20, 22, and with a non-transitory storage medium 32 that stores instructions readable and executable by the electronic data processor 30 to operate the ultrasound imaging device 10 to perform operations as disclosed herein. The electronic processor 30 may be embodied as a microprocessor or microcontroller of the US imaging device 10 (as diagrammatically indicated in FIG. 1), and/or as the microprocessor or microcontroller of a computer or other separate electronic data processing device, and/or so forth. The non-transitory storage medium 32 may, by way of non-limiting illustration, include a hard disk drive or other magnetic storage medium, a flash memory, read-only memory (ROM) or other electronic storage medium, an optical disk or other optical storage medium, various combinations thereof, or so forth.

FIG. 1 further diagrammatically depicts operations of a live ultrasound imaging process performed by the electronic processor 30 executing instructions read from the non-transitory storage medium 32. This process includes providing a live ultrasound imaging user interface (UI) 40, in which a live ultrasound image is acquired using the ultrasound imaging device 10 and the US probe 12. The live ultrasound image is displayed on the display 20. To provide context, the live ultrasound image is displayed together with a contour or reference image that is registered with the live ultrasound image using a composite transform 42. For example, for providing interventional imaging in support of a prostate biopsy procedure, the context may be a planning 3D-MRI of the prostate (or a 3D-CT image, or so forth), or may be a contour of the prostate drawn in such a 3D-MRI. The composite transform 42 may be updated occasionally by a transform update process 44, described in more detail elsewhere herein. In some embodiments, the transform update process 44 is triggered by a trigger control 46 operable by the surgeon or other user. For example, the user control panel 24 or some other user input control may operate as the trigger control 46 for triggering updates of the spatial registration 42 used to spatially register anatomical contour(s) and/or a fused 3D reference image to the live ultrasound image. It will be appreciated that the trigger control 46 may take various forms, such as a handheld remote control in wireless radio or infrared contact with the ultrasound imaging system 10, a soft key shown in the user interface display 22 (which in this case would be touch-sensitive), a dedicated trigger key on the control panel 24, or so forth.

Typically, the UI 40 implemented by the electronic processor 30 operates the ultrasound imaging device 10 to acquire and display a time series of live ultrasound images with the superimposed contour or fused reference image registered with each live ultrasound image using the composite transform. The live ultrasound images of the time series are preferably acquired at a sufficiently fast rate (i.e. "frame rate" in analogy to a video display) so that the live imaging UI 40 provides the surgeon with a near-real time view of the biopsy needle or other interventional instrument penetrating the prostate or other surgical target. In some ultrasound imaging devices, the live ultrasound images are two-dimensional (2D) live ultrasound images acquired using the US probe 12 having a one-dimensional ultrasound transducer array. In other embodiments employing an US probe with a 2D ultrasound transducer array capable of rapidly acquiring a 3D-US image, it is contemplated for the live ultrasound images to be 3D live ultrasound images.

To provide context, the live imaging UI 40 implemented by the electronic processor 30 further displays a contour or reference image together with the live ultrasound image. For example, a contour of the prostate may be superimposed on the displayed live ultrasound image depicting the prostate, and/or a 3D-MRI planning image may be fused with the live ultrasound image, e.g. using alpha blending or the like. However, cross-modality spatial registration of the 3D MRI, 3D-CT or other non-ultrasound planning image with the live ultrasound image is a computationally intensive process. Furthermore, in the case of a 2D live ultrasound image the accuracy of such spatial registration may be limited by the spatial information captured by the 2D live ultrasound image (the spatial information of a 2D live ultrasound image is limited to a plane in space). To alleviate these difficulties, a baseline three-dimensional ultrasound (3D-US) image is acquired using a 3D-US image acquisition user interface (UI) 48. Operation of the 3D-US image acquisition UI 48 depends on the particular type of the US probe 12 being employed. If the US probe 12 includes a 2D ultrasound transducer array then it can acquire a 3D-US image directly. If the US probe 12 includes only a linear ultrasound transducer array then the 3D-US image acquisition UI 48 may instruct the user to sweep the US probe 12 through a spatial distance to provide three-dimensional ultrasound echo data for generating the 3D-US image. As described elsewhere herein, the 3D-US image acquisition UI 48 is used to acquire a baseline 3D-US image and one or more reference 3D-US images with different orientations of the US probe 12 used for acquisition of the various baseline and reference 3D-US images.

It is to be appreciated that the US probe tracker 28 is provided, e.g. as an EM probe tracker that tracks the position and orientation of the US probe 12 by way of measuring spatial positions of one or more EM sensors disposed on or in the US probe 12. Each live ultrasound image is tagged with a corresponding orientation of the US probe 12 measured by the probe tracker 28 for that live ultrasound image. Likewise, each baseline 3D-US image or reference 3D-US image is tagged with a corresponding baseline or reference orientation, respectively, of the US probe 12 measured by the probe tracker 28 for that baseline or reference 3D-US image. The orientation of the US probe 12 corresponding to an US image is the orientation of the US probe 12 measured by the probe tracker 28 for the US image. This corresponding orientation is measured by the probe tracker 28 for the US image, e.g. measured during the acquisition of the US image or shortly before or after acquisition of the US image while the orientation of the US probe 12 remains that used in acquiring the US image. Each US image is tagged with the corresponding orientation of the US probe 12 measured by the probe tracker 28 for the US image. The term "tag" connotes that the corresponding orientation measured by the probe tracker 28 for the US image is associated with the US image in data storage so that the electronic processor 30 executing the instructions of the non-transitory storage medium 32 can retrieve the corresponding orientation and recognize it to be the orientation of the US probe 12 used when acquiring the corresponding US image. The tagging may, for example, be direct image tagging, e.g. the orientation may be stored as metadata contained in a header of the US image data file, or may be indirect, e.g. stored in a table, spreadsheet, or the like which indexes the US images and includes a column, field, or the like storing the corresponding orientation measured by the probe tracker 28 for each US image.

The 3D-US image acquisition UI 48 is used to acquire 3D-US images with different orientations of the US probe 12, which are used to generate a set of 3D transforms 50 used (in part) to construct the composite transform 42. More particularly, the 3D-US image acquisition UI 48 is used to acquire a baseline 3D-US image tagged with a corresponding baseline orientation measured by the probe tracker 28 for the baseline 3D-US image. A cross-modality spatial image registration process is then applied to generate a 3D transform 52, designated without loss of generality as $T_0$ herein, which registers a 3D planning image (e.g. 3D-MRI, 3D-CT image, 3D-positron emission tomography image, or so forth) with the baseline 3D-US image. This cross-modality image registration is computationally costly, and/or optionally may entail receipt of user input such as designation of corresponding landmarks in the planning image and baseline 3D-US image, respectively, or contouring of corresponding features in the planning image and baseline 3D-US image, respectively. However, the cross-modality image registration is typically performed only once for a given surgical procedure.

If the US probe 12 were to be kept in a fixed position throughout the surgical procedure, then it would be sufficient to acquire a single baseline 3D-US image and to generate the transform $T_0$ 52 registering the 3D planning image with the baseline 3D-US image. The composite transform 42 would then be a product of the transform $T_0$ and a second transform registering the baseline 3D-US image with the live ultrasound image. (Note that the term "product" as used herein in this context denotes a functional combination of $T_0$ and the second transform. This may be variously achieved, e.g. by applying $T_0$ to an image and then applying the second transform to the image).

However, during the surgical procedure, the surgeon may elect to re-position the US probe 12 to obtain a different vantage for live ultrasound imaging of the interventional instrument and target organ (e.g. biopsy needle penetrating the prostate in the case of a prostate biopsy procedure). In so doing, the re-positioned US probe may produce motion, e.g. a change in the tissue deformation produced by the US probe 12. Such motion (i.e. different tissue deformation compared with the baseline orientation of the US probe 12) is not, in general, accurately accounted for by the baseline 3D-US image.

To address this problem, in disclosed approaches the 3D-US image acquisition UI 48 is additionally used to acquire one or more reference 3D-US images each tagged with a corresponding reference orientation measured by the probe tracker 28 for that reference 3D-US image. Without loss of generality, the number of reference 3D-US images that are acquired is denoted herein as N, where N is an integer greater than or equal to one. A spatial image registration process is then applied to generate a set of 3D transforms 54, designated without loss of generality as $\{T_{1,i}\}_{i=1, \ldots, N}$ herein, where N is again the number of reference 3D-US images and the transform $T_{1,i}$ spatially registers the reference 3D-US image indexed by i with the baseline 3D-US image. (Note, where the appropriate index is apparent the employed transform may be designated by the shorthand $T_1$). As this is a same-modality (ultrasound-ultrasound) spatial registration, it is relatively low in computational cost and can in some embodiments be performed using automated feature detection processes (e.g. corner detectors or other image gradient segmentation approaches) for identifying corresponding features in the reference and baseline 3D-US images, respectively, so that the image registration can be implemented in a fully automated fashion. Alternatively, user inputs may be employed, e.g. delineating corresponding features and/or corresponding contours.

The composite transform 42 then comprises a product of at least a transform $T_{1,k}$ and a transform $T_{2,k}$. (Again, the term "product" as used herein in this context denotes a functional combination of $T_{1,k}$ and $T_{2,k}$, e.g. by applying $T_{1,k}$ to the baseline 3D-US image and then applying $T_{2,k}$ to the baseline 3D-US image after its transformation by $T_{1,k}$). This may be variously achieved, e.g. by applying $T_0$ to an image and then applying the second transform to the image). The index k here indexes a reference 3D-US image whose corresponding reference orientation should be close to the current orientation of the US probe 12 used in acquiring the current live ultrasound image. Thus, $T_{1,k}$ spatially registers the baseline 3D-US image to the reference 3D-US image indexed by k. The transform $T_{2,k}$ spatially registers the reference 3D-US image indexed by k with the live ultrasound image. Thus, the product of the transforms $T_{1,k}$ and $T_{2,k}$ operates to spatially register the baseline 3D-US image to the current live ultrasound image. If the contour or reference image to be displayed together with the live ultrasound image is the 3D planning image or a contour drawn in the 3D planning image, then the composite transform 42 further includes the transform $T_0$, i.e. the composite transform 42 comprises the product of the transform $T_0$, the transform $T_{1,k}$, and the transform $T_{2,k}$. (Yet again, the term "product" as used herein in this context denotes a functional combination of $T_0$, $T_{1,k}$ and $T_{2,k}$, e.g. by applying $T_0$ to the planning image or to a contour drawn in the planning image to transform to the spatial frame of the baseline 3D-US image, and then applying $T_{1,k}$ to transform to the spatial frame of the reference 3D-US image indexed by k, and then applying $T_{2,k}$ to transform to the spatial frame of the live ultrasound image).

(In some embodiments, it is contemplated that the reference contour or reference image to be displayed together with the live ultrasound image may be the baseline 3D-US image or a contour drawn in the baseline 3D-US image. In this case, the composite transform 42 would not include $T_0$, and indeed in such embodiments there may be no 3D planning image acquired by a modality other than ultrasound.)

With the framework described above with reference to FIG. 1, updating the composite transform 42 to account for a re-positioning of the US probe 12 entails determining the closest reference orientation of the US probe 12 to a current orientation of the US probe 12 measured by the probe tracker 28. In the composite transform 42, $T_{1,k}$ is updated by setting k equal to the index of the reference 3D-US image with that closest reference orientation. For displaying live images subsequent to this updating, $T_{2,k}$ is constructed to spatially register the reference 3D-US image indexed by updated k with the live ultrasound image. The transform $T_0$ (if employed) is not modified by this update, thus advantageously avoiding the computational cost of re-computing the transform $T_0$.

Figure 2:
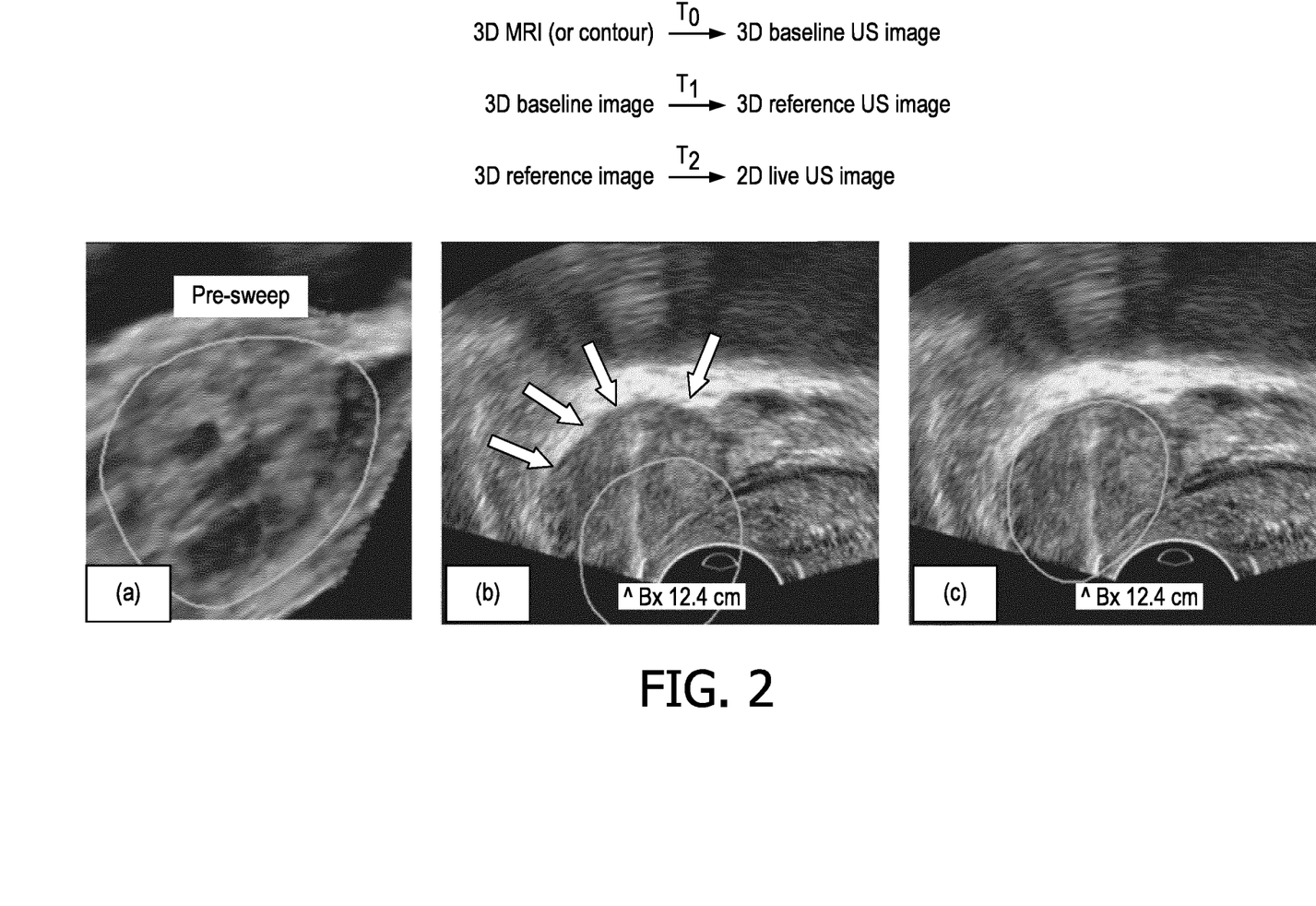
FIG. 2 shows representative images with tissue motion correction suitably produced by the US-guidance portion of the US-guided prostate biopsy system of FIG. 1.

With reference to FIG. 2, the effect of such an update is shown. FIG. 2, lefthand image, depicts a baseline 3D-US image of a prostate with a contour superimposed. In this illustrative example, the contour is drawn in the baseline 3D-US image, but alternatively it may be a contour drawn in a 3D planning image such as a 3D-MRI and transformed to the spatial frame of the baseline 3D-US image using the transform $T_0$. FIG. 2, middle image, depicts a 2D live ultrasound image with the contour of FIG. 1, transformed by the transform $T_{1,k}$ and $T_{2,k}$ to the spatial frame of the 2D live ultrasound image. However, as seen in FIG. 2, there is a large mismatch between the contour and the boundary of the prostate in the 2D live ultrasound image (indicated by arrows in FIG. 2, middle image). FIG. 2, right image, shows the same 2D live ultrasound image with an updated contour which is updated by updating the composite transform to employ the transform $T_{1,k}$ with k updated to the closest reference 3D-US image. FIG. 2 also indicates the successive application of the transforms $T_0$, $T_1$, and $T_2$ suitable for implementing the composite transform comprising the product of the transforms $T_0$, $T_1$, and $T_2$.

It may be noted that in a limiting case, it may be that the closest reference orientation to the current orientation of the US probe 12 is actually the baseline orientation corresponding to the baseline 3D-US image, rather than to any of the reference 3D-US images. In such a case, the transform $T_1$ may be omitted or, from an alternative viewpoint, the transform $T_1$ may be set to a unity transform such that applying unity transform $T_1$ to the baseline 3D-US image outputs the same baseline 3D-US image without modification.

The baseline orientation is preferably chosen to be the orientation most commonly used in performing the surgical procedure. For example, in the case of a prostate biopsy, the baseline orientation may preferably be an axial orientation. The additional reference volumes (reference 3D-US images) are obtained in the same region of interest as the baseline 3D-US image, but with different probe orientations that may induce different tissue deformation and thereby different image appearance. The reference volumes are registered to the baseline volume to map image voxels in the reference volume to image voxels in the baseline volume. Since these are volumetric registrations, a significant amount of image information can advantageously be used for registration, which enables determining the transforms $\{T_{1,i}\}_{i=1,\ldots,N}$ 54 accurately and robustly, despite the deformation-induced differences between the volumes.

Figure 3:
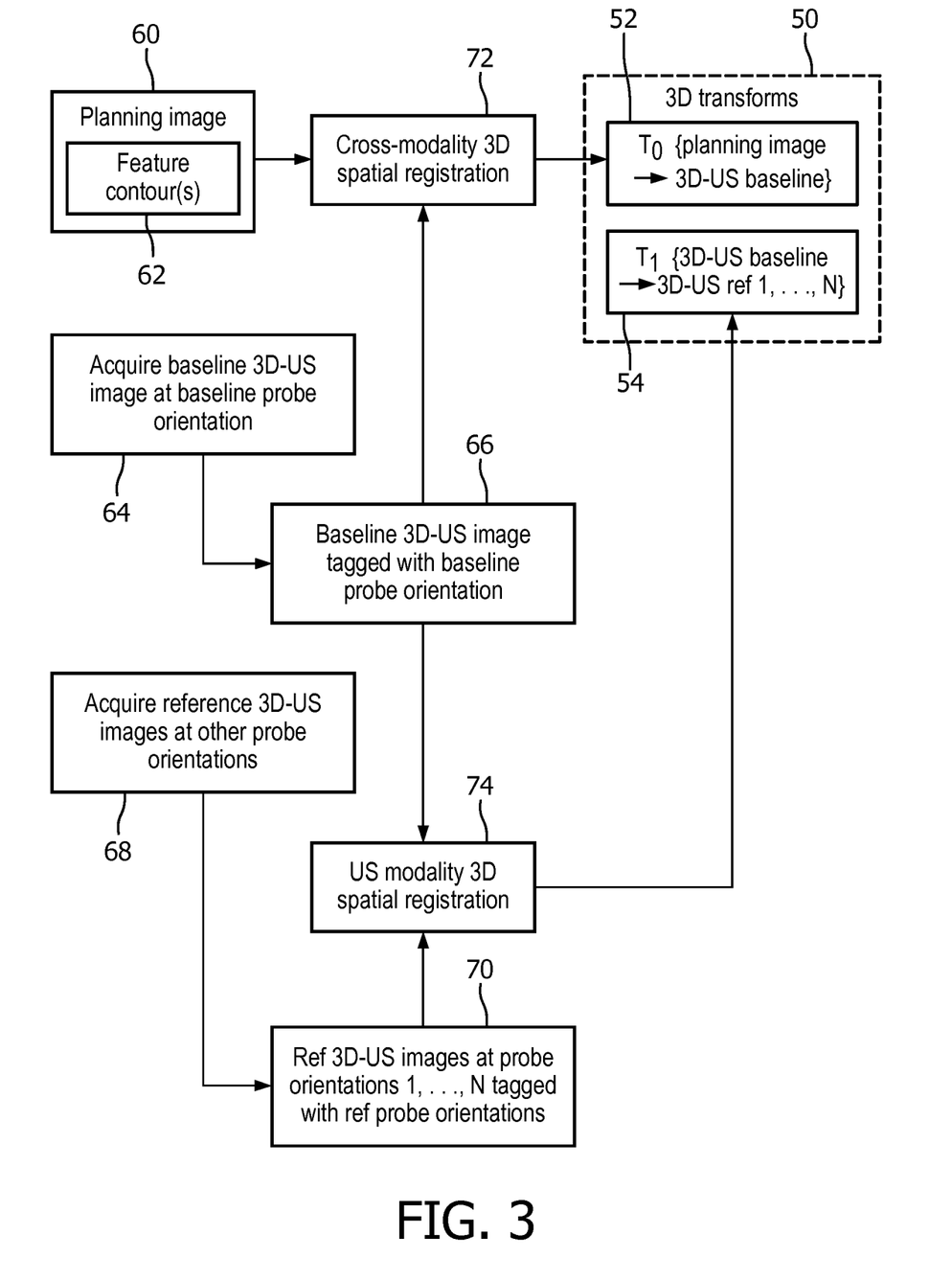
FIG. 3 diagrammatically shows acquisition and processing of 3D baseline and reference US images performed by the US-guided prostate biopsy system of FIG. 1.

With continuing reference to FIG. 1 and with further reference to FIG. 3, a process suitably performed by the electronic processor 30 executing instructions read from the non-transitory storage medium 32 to generate the 3D transforms 50 is described. The process receives a 3D planning image 60, and optionally also receives one or more feature contours 62 drawn in the planning image 60 (if such contours are to be superimposed onto the live ultrasound image). An operation 64 performed by the 3D-US image acquisition UI 48 acquires a baseline 3D-US image 66 tagged with a corresponding baseline orientation of the US probe 12 measured by the probe tracker 28 for the baseline 3D-US image 66. An operation 68 performed by the 3D-US image acquisition UI 48 acquires one or more reference 3D-US images 70 (i.e. N such images) each tagged with a corresponding reference orientation of the US probe 12 measured by the probe tracker 28 for that reference 3D-US image. (It will be appreciated that the operations 64, 68 may be performed with various ordering). An operation 72 applies a cross-modality image registration to register the planning image 60 (and hence the contour 62, if drawn in the planning image 62) with the baseline 3D-US image 66. This generates the transform $T_0$ 52. An operation 74 applies a same-modality (ultrasound-ultrasound) image registration to register the baseline 3D-US image 66 with each reference 3D-US image of the one or more reference 3D-US images 70. This generates the set of transforms $\{T_{1,i}\}_{i=1,\ldots,N}$ 54.

Figure 4:
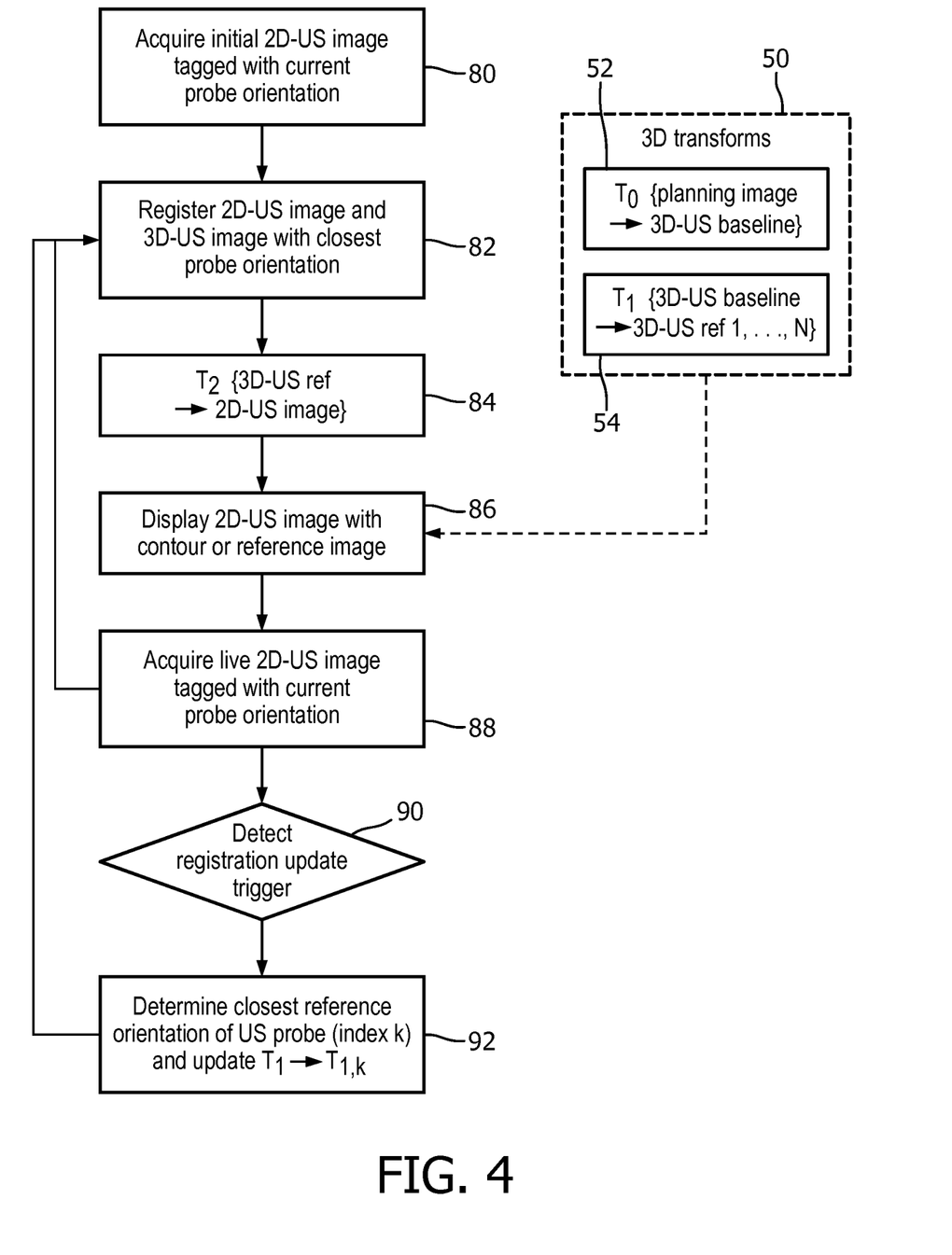
FIG. 4 diagrammatically shows live US imaging performed in support of a prostate biopsy surgical procedure by the US-guidance portion of the US-guided prostate biopsy system of FIG. 1.

With continuing reference to FIG. 1 and with further reference to FIG. 4, a process suitably performed by the electronic processor 30 executing instructions read from the non-transitory storage medium 32 to perform the live ultrasound imaging including the update 44 of the composite transform 42 in response to activation of the trigger control 46 is described. In the example of FIG. 4, the live ultrasound images are assumed to be 2D live ultrasound images. In an operation 80, an initial 2D live ultrasound image is acquired and tagged with its corresponding orientation of the US probe 12. In an operation 82, the 2D live ultrasound image is spatially registered with the closest reference (or baseline) 3D-US image to generate the transform $T_2$ 84, and the 2D live ultrasound image is displayed in an operation 86 together with the contour or reference image. Thereafter, a time series of 2D live images is generated by iterating the steps 82, 84, 86, 88. As this time series live imaging is performed, the user may elect to re-position the US probe 12 causing the initially chosen closest 3D-US image to no longer be sufficiently accurate (e.g. as shown in FIG. 2, middle image). When the user recognizes this degrading accuracy, the user may activate the update trigger 46 which is detected in an operation 90. In an operation 92 the current orientation of the US probe 12 as measured by the probe tracker 28 is compared with the reference orientations and the baseline orientation, and the closest reference orientation (indexed k herein, without loss of generality) is selected. Flow then passes back to operation 82 to continue the live ultrasound imaging using the updated closest 3D-US reference image indexed k (i.e. the transform $T_1$ is updated to the index k and the transform $T_2$ is updated to $T_{2,k}$ by registering the 2D live ultrasound image and the updated closest reference 3D-US image indexed k).

Although not shown in FIG. 4, optionally, if additional reference orientations are needed that were not acquired in the setup process (FIG. 3), the live ultrasound imaging time series production (i.e. iteration of operations 82, 84, 86, 88) may be interrupted and one or more additional reference 3D-US images with the additional reference orientations may be acquired and registered with the baseline 3D-US image as per operations 68, 74 of FIG. 3. If the initial set of transforms is $\{T_{1,i}\}_{i=1,\ldots,N}$ 54, then the new transform for the additional reference orientation may be suitably denoted as $T_{1,N+1}$. Such a new reference 3D-US image acquisition may be triggered, for example, if in the operation 92 the closest reference orientation of the US probe 12 is different from the current orientation of the US probe 12 by more than a threshold amount. As previously noted, if the US probe 12 has only a linear array of ultrasound transducers, operating the ultrasound imaging device to acquire the new reference 3D-US image may include prompting the user to manually manipulate the US probe 12 to perform a designated sweep of the US probe 12 during the acquisition of the new reference 3D-US image.

In the illustrative embodiments (e.g. FIG. 1), the transform update 44 is triggered manually by user operation of the trigger control 46. In alternative embodiments, it is contemplated to automatically trigger the transform update 44 upon detection of a trigger condition. For example, an update may be triggered if, in the operation 82, a fit quality metric for the spatially registered images indicates a low accuracy of the spatial registration.

In the illustrative implementations of the transform update 44, a single live ultrasound image is taken as the current live ultrasound image. In alternative embodiments, the current live ultrasound image may comprises a plurality of live ultrasound images of the time series of live ultrasound images acquired with the same current orientation. Thus, for example, the registration operation 82 may optimally register the plurality of live ultrasound images with best accuracy averaged over the plurality of live ultrasound images. Such an approach can improve accuracy and reduce the likelihood of spurious results due to an outlier 2D live ultrasound image having substantial noise or other image artifact(s).

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. An interventional imaging device comprising:
   an ultrasound probe;
   an ultrasound imaging device operatively connected with the ultrasound probe to perform ultrasound imaging using the ultrasound probe;
   a display;
   a probe tracker operative to track orientation of the ultrasound probe;
   an electronic processor operatively connected with the ultrasound imaging device, the probe tracker, and the display; and
   a non-transitory storage medium storing instructions readable and executable by the electronic data processor to operate the ultrasound imaging device to acquire a live ultrasound image and to operate the display to display the live ultrasound image together with a contour or reference image that is registered with the live ultrasound image using a composite transform the composite transform comprising a function combination of two or more transforms, and to perform further operations including:
   operating the ultrasound imaging device to acquire a baseline three-dimensional ultrasound (3D-US) image tagged with a corresponding baseline orientation of the ultrasound probe measured by the probe tracker for the baseline 3D-US image;
   operating the ultrasound imaging device to acquire one or more reference 3D-US images each tagged with a corresponding reference orientation of the ultrasound probe measured by the probe tracker for the reference 3D-US image;
   computing a transform to spatially register each reference 3D-US image with the baseline 3D-US image;
   determining a closest reference 3D-US image whose corresponding orientation is closest to a current orientation of the ultrasound probe measured by the probe tracker; and
   updating the composite transform to include the transform to spatially register the closest reference 3D-US image to the baseline 3D-US image.

2. The interventional imaging device of claim 1 wherein:
   the operation of computing a transform to spatially register each reference 3D-US image with the baseline 3D-US image computes a set of transforms $\{T_{1,i}\}_{i=1, \ldots, N}$ where N is the number of reference 3D-US images and the transform $T_{1,i}$ spatially registers the reference 3D-US image indexed by i with the baseline 3D-US image; and
   the updating of the composite transform comprises updating the composite transform to a product of at least a transform $T_{1,k}$ and a transform $T_{2,k}$ where k indexes the determined closest reference 3D-US image and the transform $T_{2,k}$ spatially registers the determined closest reference 3D-US image with the live ultrasound image.

3. The interventional imaging device of claim 2 wherein:
   the updated composite transform comprises a product of a transform $T_0$ and the transform $T_{1,k}$ and the transform $T_{2,k}$ where the transform $T_0$ spatially registers a three-dimensional planning image acquired by an imaging modality other than ultrasound with the baseline 3D-US image; and
   the updating of the composite transform does not update the transform $T_0$.

4. The interventional imaging device of claim 3 wherein the three-dimensional planning image acquired by an imaging modality other than ultrasound comprises a three-dimensional magnetic resonance image (3D-MRI) or a three-dimensional computed tomography (3D-CT) image.

5. The interventional imaging device of claim 3 wherein the contour or reference image that is displayed together with the live ultrasound image comprises a contour defined in the planning image and registered with the baseline 3D-US image using the transform $T_0$.

6. The interventional imaging device of claim 2 wherein the electronic processor operates the ultrasound imaging device to acquire and display a time series of live ultrasound images together with the contour or reference image registered with the live ultrasound images using the composite transform, and wherein:
   the transform $T_{2,k}$ of the updated composite transform is generated for the live ultrasound images acquired subsequent to the updating of the composite transform by spatially registering the determined closest reference 3D-US image indexed by k with the live ultrasound image.

7. The interventional imaging device of claim 1 wherein the updating of the composite transform is triggered by detection of user activation of a trigger control.

8. A non-transitory storage medium storing instructions readable and executable by an electronic processor that is in operative communication with an ultrasound imaging device with an ultrasound probe and with a display and with a probe tracker operative to track orientation of the ultrasound probe, the instructions readable and executable by the electronic processor to perform a live imaging method including:
   operating the ultrasound imaging device to acquire a live ultrasound image;
   spatially registering a contour or reference image with the live ultrasound image using a composite transform, the composite transform comprising a function combination of two or more transforms;
   displaying the live ultrasound image together with the spatially registered contour or reference image on the display; and
   adjusting the composite transform by operations including:
   operating the ultrasound imaging device to acquire a baseline three-dimensional ultrasound (3D-US) image tagged with a corresponding baseline orientation of the ultrasound probe measured by the probe tracker for the baseline 3D-US image;
   operating the ultrasound imaging device to acquire one or more reference 3D-US images each tagged with a corresponding reference orientation of the ultrasound probe measured by the probe tracker for the reference 3D-US image;
   computing a set of transforms $\{T_{1,i}\}_{i=1, \ldots, N}$ to spatially register the reference 3D-US images with the baseline 3D-US image where N is the number of reference 3D-US images and the transform $T_{1,i}$ spatially registers the reference 3D-US image indexed by i with the baseline 3D-US image;

determining a closest reference orientation which is closest to a current orientation of the ultrasound probe measured by the probe tracker; and updating the composite transform to a product of at least a transform $T_{1,k}$ and a transform $T_{2,k}$ where k indexes the determined closest reference 3D-US image whereby the transform $T_{1,k}$ spatially registers the determined closest reference 3D-US image indexed by k with the baseline 3D-US image and the transform $T_{2,k}$ spatially registers the determined closest reference 3D-US image with the live ultrasound image.

9. The non-transitory storage medium of claim 8 wherein:

the updating updates the composite transform to a product of a transform $T_0$ and the transform $T_{1,k}$ and the transform $T_{2,k}$ where the transform $T_0$ spatially registers a three-dimensional planning image acquired by an imaging modality other than ultrasound with the baseline 3D-US image; and the contour or reference image that is displayed together with the live ultrasound image is the planning image or a contour defined in the planning image.

10. The non-transitory storage medium of claim 8 wherein the operations of operating the ultrasound imaging device to acquire the live ultrasound image, spatially registering the contour or reference image with the live ultrasound image, and displaying the live ultrasound image together with the spatially registered contour or reference image are repeated iteratively to acquire and display a time series of live ultrasound images together with the contour or reference image registered with the live ultrasound images using the composite transform.

11. The non-transitory storage medium of claim 10 wherein the operations of operating the ultrasound imaging device to acquire the baseline 3D-US image, operating the ultrasound imaging device to acquire the one or more reference 3D-US images, and computing the set of transforms $\{T_{1,i}\}_{i=1,\ldots,N}$ are performed prior to the acquiring and displaying of the time series of live ultrasound images.

12. The non-transitory storage medium of claim 11 wherein the updating of the composite transform is by operations further including:

interrupting the acquiring and displaying of the time series of live ultrasound images to operate the ultrasound imaging device to acquire a new reference 3D-US image tagged with the corresponding reference orientation and computing a new transform $T_{1,N+1}$ that spatially registers the new reference 3D-US image with the baseline 3D-US image;

wherein if the determined closest reference orientation corresponds to the new reference 3D-US image then the composite transform is updated to a product of at least the transform $T_{1,N+1}$ and a transform $T_{2,N+1}$ the transform $T_{2,N+1}$ spatially registers the new reference 3D-US image with the live ultrasound image.

13. The non-transitory storage medium of claim 12 wherein the operating of the ultrasound imaging device to acquire the new reference 3D-US image includes prompting a user to manually manipulate the ultrasound probe to perform a designated sweep of the ultrasound probe during the acquisition of the new reference 3D-US image.

14. The non-transitory storage medium of claim 8 wherein the adjusting of the composite transform is triggered by detection of user activation of a trigger control.

15. The non-transitory storage medium of claim 8 wherein the operating of the ultrasound imaging device to acquire the live ultrasound image comprises:

operating the ultrasound imaging device to acquire the live ultrasound image consisting of a two-dimensional ultrasound image.

\* \* \* \* \*